(12) United States Patent
Krill et al.

(10) Patent No.: US 11,427,664 B2
(45) Date of Patent: Aug. 30, 2022

(54) PROCESS FOR PRODUCING OPTICAL MOLDING MATERIALS

(71) Applicant: Röhm GmbH, Darmstadt (DE)

(72) Inventors: Steffen Krill, Muehltal (DE); Belaid Ait Aissa, Darmstadt (DE); Florian Zschunke, Frankfurt (DE); Gerhard Kölbl, Gernsheim (DE); Rüdiger Carloff, Darmstadt (DE)

(73) Assignee: Röhm GmbH, Darmstadt (DE)

( * ) Notice: Subject to any disclaimer, the term of this patent is extended or adjusted under 35 U.S.C. 154(b) by 342 days.

(21) Appl. No.: 16/637,575

(22) PCT Filed: Aug. 20, 2018

(86) PCT No.: PCT/EP2018/072419
§ 371 (c)(1),
(2) Date: Feb. 7, 2020

(87) PCT Pub. No.: WO2019/042807
PCT Pub. Date: Mar. 7, 2019

(65) Prior Publication Data
US 2021/0032386 A1    Feb. 4, 2021

(30) Foreign Application Priority Data

Aug. 29, 2017 (EP) .................... 17188252

(51) Int. Cl.

| | | |
|---|---|---|
| C08F 220/14 | (2006.01) | |
| C07C 45/75 | (2006.01) | |
| C07C 67/39 | (2006.01) | |
| C07C 67/48 | (2006.01) | |
| C08F 2/01 | (2006.01) | |
| C08F 2/06 | (2006.01) | |
| C07C 47/22 | (2006.01) | |
| C07C 69/54 | (2006.01) | |
| C08F 2/00 | (2006.01) | |

(52) U.S. Cl.
CPC ............ *C08F 220/14* (2013.01); *C07C 45/75* (2013.01); *C07C 67/39* (2013.01); *C07C 67/48* (2013.01); *C08F 2/001* (2013.01); *C08F 2/06* (2013.01); *C07C 47/22* (2013.01); *C07C 69/54* (2013.01)

(58) Field of Classification Search
USPC ................................................ 526/75, 329.7
See application file for complete search history.

(56) References Cited

U.S. PATENT DOCUMENTS

| | | | |
|---|---|---|---|
| 5,969,178 A | 10/1999 | Okamoto et al. | |
| 6,765,046 B1 * | 7/2004 | Numrich | C08K 5/0041 |
| | | | 524/416 |
| 7,012,039 B2 | 3/2006 | Watanabe et al. | |
| 8,669,338 B2 | 3/2014 | Carloff et al. | |
| 9,617,199 B2 | 4/2017 | Krill et al. | |
| 9,890,105 B2 | 2/2018 | Krill et al. | |
| 9,963,417 B2 | 5/2018 | Krill et al. | |
| 10,273,201 B2 | 4/2019 | Krill et al. | |
| 10,301,251 B2 | 5/2019 | Groemping et al. | |
| 10,457,626 B2 | 10/2019 | Krill et al. | |
| 2012/0172563 A1 | 7/2012 | Carloff et al. | |
| 2016/0068464 A1 | 3/2016 | Krill et al. | |
| 2016/0251301 A1 | 9/2016 | Krill et al. | |
| 2016/0280628 A1 | 9/2016 | Krill et al. | |
| 2018/0050977 A1 | 2/2018 | Krill et al. | |
| 2018/0251419 A1 | 9/2018 | Groemping et al. | |
| 2019/0077742 A1 | 3/2019 | Krill et al. | |
| 2019/0112255 A1 | 4/2019 | Krill et al. | |

FOREIGN PATENT DOCUMENTS

| | | |
|---|---|---|
| WO | 2011/051032 | 5/2011 |
| WO | 2014/170223 | 10/2014 |
| WO | 2017/046110 | 3/2017 |

OTHER PUBLICATIONS

International Search Report dated Oct. 23, 2018 in PCT/EP2018/072419 with English translation (7 pages).
Written Opinion dated Oct. 23, 2018 in PCT/EP2018/072419.
U.S. Pat. No. 9,890,105, Feb. 13, 2018, 2016/0068464, Krill et al.
U.S. Pat. No. 10,273,201, Apr. 30, 2019, 2018/0050977, Krill et al.
U.S. Pat. No. 10,457,626, Oct. 29, 2019, 2019/0077742, Krill et al.
U.S. Appl. No. 16/161,395, filed Oct. 16, 2018, 2019/0112255, Krill et al.
U.S. Pat. No. 9,617,199, Apr. 11, 2017, 2016/0251301, Krill et al.
U.S. Pat. No. 9,963,417, May 8, 2018, 2016/0280628, Krill et al.
U.S. Pat. No. 10,301,251, May 28, 2019, 2018/0251419, Groemping et al.
U.S. Appl. No. 16/611,546, filed Nov. 7, 2019, Lygin et al.
English translation of the Written Opinion dated Oct. 23, 2018 in PCT/EP2018/072419, 6 pages.

* cited by examiner

*Primary Examiner* — Fred M Teskin

(74) *Attorney, Agent, or Firm* — Grüneberg and Myers PLLC

(57) ABSTRACT

A process is useful for producing optical molding materials on the basis of methyl methacrylate (MMA), wherein this MMA has been produced by an optimized method and the molding materials feature in particular a very low yellowness index. This MMA has been produced by direct oxidative esterification of methacrolein. In particular, an optimized workup of the reactor output from the oxidative esterification of methacrolein is useful for removing particularly discoloring byproducts. This process moreover has the advantage that fewer demands than described in related art are placed on plant apparatus configuration.

17 Claims, No Drawings

PROCESS FOR PRODUCING OPTICAL MOLDING MATERIALS

CROSS-REFERENCE TO RELATED APPLICATIONS

This application is a National Stage entry under § 371 of International Application No. PCT/EP2018/072419, filed on Aug. 20, 2018, and which claims the benefit of European Application No. 17188252.5, filed on Aug. 29, 2017, both of which are incorporated by reference in their entireties.

BACKGROUND OF THE INVENTION

Field of the Invention

The present invention relates to a process for producing optical molding materials on the basis of methyl methacrylate, wherein this MMA has been produced by an optimized method and the molding materials feature in particular a very low yellowness index. This MMA employed according to the invention has been produced by direct oxidative esterification of methacrolein.

In particular the present invention relates to an optimized workup of the reactor output from the oxidative esterification of methacrolein by means of which particularly discoloring byproducts are removed. This process moreover has the advantage that fewer demands than described in the prior art are placed on plant apparatus configuration.

Discussion of the Background

Methyl methacrylate is used in large amounts for preparing polymers and copolymers with other polymerizable compounds. In addition, methyl methacrylate is an important synthesis unit for a variety of specialty esters based on methacrylic acid (MAA) which can be produced by transesterification with the appropriate alcohol. There is consequently a great interest in very simple, economic and environmentally friendly processes for preparing this starting material. It is of particular interest, to provide MMA or other alkyl methacrylates which in the polymer for example for processing into the molding material result in particularly low yellow discoloration.

Methyl methacrylate (MMA) is currently produced by a variety of processes proceeding from $C_2$, $C_3$ or $C_4$ synthesis units. In one process which is said to be particularly efficient MMA is obtained by gas-phase oxidation of isobutylene or tert-butanol with atmospheric oxygen over a heterogeneous catalyst to afford methacrolein and subsequent oxidative esterification of methacrolein using methanol. This process, developed by ASAHI, is described, inter alia, in publications U.S. Pat. Nos. 5,969,178 and 7,012,039. A particular disadvantage of this process is the very high energy requirement. In a development of the process the methacrolein is obtained from propanal and formaldehyde in the first stage. Such a process is described in WO 2014/170223.

U.S. Pat. No. 5,969,178 describes such a process for oxidative conversion of isobutene or tert-butanol into methacrolein and subsequent oxidative esterification to MMA. In this second stage a liquid mixture of methacrolein and methanol with reduced water content is reacted with molecular oxygen and a palladium catalyst, wherein said palladium catalyst is usually in supported form as a palladium-lead catalyst. In a first distillation stage a mixture of methacrolein and methanol is then removed from the crude product of the oxidative esterification below the top of the column while low-boiling constituents are removed overhead. The MMA-containing bottoms product is then passed into a second distillation stage in which an azeotrope of methanol and saturated hydrocarbons is removed overhead. The bottoms product comprising the crude MMA is sent to a further workup while methanol is isolated from the overhead fraction by means of a phase separator and a third distillation column and passed back into the reactor. It is to be borne in mind that the methanol can contain relatively large amounts of water on account of the azeotrope formed and must therefore be sent to a dewatering.

As an alternative to this process U.S. Pat. No. 5,969,178 discloses a workup in only one column wherein in said column it is imperative that the feed be situated above the column bottom. Low-boiling constituents from the reactor output are removed from this column overhead. Remaining in the column bottom is a mixture of crude MMA and water which is to be sent to a further workup. Via a sidestream whose exact position must first be determined, said position being adjustable by addition of various sieve trays, a mixture of methacrolein and methanol intended for returning into the reactor is finally taken off from the column. U.S. Pat. No. 5,969,178 itself indicates that such a process is difficult to perform on account of a variety of azeotropes. Particularly methacrylic acid, which is always present as a byproduct, moreover plays an important role. According to this process, despite the silence of U.S. Pat. No. 5,969,178 on this issue, the methacrylic acid would be removed in a manner such that it remains in a phase to be sent for disposal and an isolation would be of only limited attractiveness. However, this results in a fall in the overall yield of methacrylic products of this process.

U.S. Pat. No. 7,012,039 discloses a workup of the reactor output from the oxidative esterification which is somewhat of a departure. Here, in a first distillation stage methacrolein is distilled overhead via sieve trays and the aqueous, MMA-containing mixture from the bottom is passed into a phase separator. In said phase separator the mixture is pH-adjusted to a pH of about 2 by addition of sulfuric acid. The separation of the sulfuric-acid-acidified water from the organic/oil phase is then effected by means of centrifuging. This oil phase is separated in a further distillation into high-boiling constituents and an MMA-containing phase withdrawn overhead. The MMA-containing phase is then separated from low-boiling constituents in a third distillation. This is even followed by a fourth distillation for final purification.

The problem with this process is the sulfuric acid which needs to be added in large amounts and can have corrosive effects on parts of the plant. Accordingly these parts, such as in particular the phase separator or else the second distillation column, must be fabricated from suitable materials. Moreover, U.S. Pat. No. 7,012,039 is silent regarding the handling of the simultaneously generated methacrylic acid or the residual methanol remaining in the product. However it can be assumed that the former is coremoved in the distillation stages while the methanol can be obtained and returned with the methacrolein only partially while the remainder is probably lost in the third distillation stage.

WO 2014/170223 describes a similar process to U.S. Pat. No. 7,012,039. The only difference is that in the actual reaction the pH is adjusted in a circuit by addition of a methanolic sodium hydroxide solution. This serves, inter alia, to protect the catalyst. Moreover, the removal of the aqueous phase in the phase separation is simpler on account of the salt content. However, another consequence is that the methacrylic acid formed is in the form of sodium salt and is later removed and disposed of with the aqueous phase. Admittedly, in the variant where sulfuric acid is added in the phase separation the free acid is recovered. However, instead, sodium (hydrogen) sulfate is generated which can lead to other problems upon disposal.

Finally, WO 2017/046110 teaches an optimized workup of the crude MMA obtained from an oxidative esterification is initially separated from a heavy phase and subsequently distilled off from this heavy phase is an alcohol-containing light phase which in turn can be recycled. What is also special about this process is that here the methacrolein has been obtained on the basis of propanal and formaldehyde, wherein the former is obtained on the basis of C2 synthesis units, for example from ethylene and synthesis gas.

However, independently of the raw material basis for the employed methacrolein all of these processes result overall in MMA or in general alkyl methacrylates that result in yellow discoloration of descendent products, for example molding materials. There is thus a need for improvement of the kind where the source of this yellow discoloration is identified and before polymerization removed from the relevant alkyl methacrylate, in particular MMA, as efficiently as possible.

SUMMARY OF THE INVENTION

In view of the prior art the problem addressed by the present invention is therefore that of providing a technically improved process for producing polymer resins having a particularly low yellow discoloration.

A particular problem addressed was that of providing the alkyl methacrylates, in particular MMA, used for producing these polymer resins on the basis of an oxidative esterification of methacrolein.

A further problem addressed by the present invention was that of identifying and efficiently removing from the alkyl methacrylate the byproducts which are formed in the oxidative esterification of methacrolein and result in yellow discoloration of descendent products.

A further particular problem addressed was that of providing a process that can be operated with the lowest possible disposal cost, in particular through reduced generation of organic constituents and acids in the waste stream.

The process shall furthermore be inexpensive, in particular in terms of the materials to be employed for construction of the plant, compared to the prior art.

DETAILED DESCRIPTION OF THE INVENTION

These problems were solved by developing a novel process for producing alkyl methacrylate resins. This process comprises the steps of:
a. production of methacrolein in a reactor I,
b. oxidative esterification of the methacrolein in the presence of an alcohol, oxygen and a heterogeneous noble metal-containing catalyst at a water content between 0.1% and 10% by weight and a pH between 5 and 8, preferably between 6 and 8, in at least one reactor II,
c. aftertreatment of the reactor output from reactor II in a reactor III,
d. isolation and purification of the crude alkyl methacrylate from reactor III and
e. polymerization of the alkyl methacrylates from process step d or a mixture containing alkyl methacrylates from process step d to obtain an alkyl methacrylate resin.

It should be noted that the individual process steps need not be performed in continuous immediately consecutive fashion. Further process steps, for example intermediate purifications, may also be performed between the recited steps a to e. It is preferable when the process steps a to d, optionally supplemented by intermediate steps, are effected consecutively in the specified sequence and in continuous operation. By contrast, process step e may be performed in marked spatial and temporal separation from the other steps after an optional additional purification, transport and/or storage, weeks or even months after the monomer synthesis of steps a to d.

According to the invention the present invention has the particular feature that in process step c in reactor III the water content is at least 0.5% by weight, preferably at least 0.75% by weight, especially preferably at least 1% by weight, higher than in reactor II. In addition the alcohol concentration in process step c in reactor III is lower than in reactor II in which process step b is performed. Finally, this novel process is characterized in that the pH in reactor III is between 0.5 and 7, in particular between 0.5 and 6, and is thus set at least 0.5 lower than in reactor II.

In principle the methacrolein in process step a in reactor I may be produced on the basis of C2- or C4-synthesis units. It is preferable when process step a is the reaction of propanal with formaldehyde in the presence of at least one acid and optionally an amine, i.e. a process step proceeding from C2-synthesis units. In particular the process according to the invention may be applied to the combinations of such a C2-based process for producing methacrolein and a subsequent oxidative esterification to afford an alkyl methacrylate in process step b. This relates in particular to the descriptions of a combination of process steps a and b such as may be found for example in DE 3 213 681, U.S. Pat. No. 4,408,079, CN 1 038 461 04 or in European patent application having filing number 14185345.7.

It is preferable when the alcohol in process step b is methanol and the alkyl methacrylate obtained as a crude product from this process step is accordingly MMA.

It is preferable when in process step c an organic and/or a mineral acid are added to the reactor III to adjust the pH. Simultaneously or independently and likewise preferably dimethoxyisobutene is cleaved with water to afford methacrolein and methanol in this reactor III.

The acid addition may be effected such that it is passed directly into reactor III. However, the acid may alternatively also be supplied to the feed from for example reactor II into reactor III. Also possible is that the crude product from reactor II is first provided with the acid in a mixing chamber before feeding of this mixture into the reactor III is effected.

It is especially preferable when the process according to the invention in terms of process step c is characterized in that to adjust the pH sulfuric acid is added to reactor III and in that the liquid phase in reactor III has a temperature between 0° C. and 140° C. This internal temperature measured in the liquid phase depends in particular on the precise configuration of the employed reactor. According to the invention there are in terms of the precise configuration of the reactor III four particularly preferred embodiments:

In the first embodiment reactor III is a distillation column. In this case the acid, optionally together with additional water, is preferably introduced into the bottom of this distillation column. Present in these column bottoms are inter alia liquid methacrolein and portions of the remaining alcohol which are separated from the crude alkyl methacrylate at a temperature between 50° C. and 100° C.

In the second preferred embodiment of the process step c reactor III is a phase separator into whose aqueous phase the acid and optionally additional water are introduced. In this phase separator an aqueous phase containing the remaining alcohol is separated from an organic phase containing the alkyl methacrylate at a temperature between 0° C. and 100° C.

In the third preferred embodiment of the process step c reactor III is a tubular reactor in which the reactor output from reactor II having an internal temperature between 50° C. and 140° C. the acid and optionally additional water are mixed. This mixture may subsequently be passed into a distillation column or a phase separator.

In the fourth preferred embodiment of the process step c reactor III is a continuously operated stirred reactor. In this reactor too, similarly to the previously described tubular reactor, the reactor output from reactor II is mixed with the acid and optionally additional water at an internal temperature between 50° C. and 140° C. Subsequently this mixture is preferably passed into a distillation column or a phase separator.

The precise configuration of the process step d is easily deducible for those skilled in the art, in particular in view of the precise configuration of the preceding process steps. A series of different purification stages preferably but not necessarily serially connected, may be employed. It is particularly preferable when the isolation and purification stages are at least one optional phase separator, at least one high boiler column, at least one low boiler column and optionally at least one crystallization chamber. It is particularly preferable when these apparatuses are traversed in series.

A further important process step is process step e, the polymerization of the product from process step d. In respect of process step e there are naturally many alternative embodiments. Thus in process step e from the alkyl methacrylate or from a mixture containing at least one alkyl methacrylate from process step d a polymer or a mixture containing a polymer may be produced. Such a mixture may be for example an only partially polymerized monomer mixture, for example in the form of a syrup or a so-called MoPo (monomer-polymer system). The polymerization may be effected for example by means of bulk, emulsion, suspension or solution polymerization. The polymerization is generally a free-radical polymerization. However, it is also possible to employ another polymerization such as an anionic or for example a group-transfer polymerization.

According to the invention the polymerization produces an alkyl methacrylate resin which may for example be subsequently processed into a molding material or in admixture with other components processed into a molding material.

Polymer resins are polymers thermoplastically deformable through choice of a suitable temperature. Depending on the molecular weight of the polymer chains of the polymer, the polymer proportion in the polymer resin and any partial crosslinking of the polymer chains the forming temperature for alkyl methacrylate polymers may be greater than 320° C. Should polymerization of alkyl methacrylates be effected in the presence of crosslinking monomers or substances the proportion of polymer chains crosslinked with one another generally increases. The required temperature for thermoplastic forming of the polymer resin will thus increase. At very high contents of crosslinker monomers or substances which result in crosslinking the required forming temperature increases as far as the range of thermal degradation of the polymer resin.

According to the invention "polymer resin" is to be understood as also encompassing systems of the type previously recited but which have been only partially polymerized.

According to the invention the to-be-polymerized compositions may contain not only the above alkyl methacrylates produced according to the invention by process steps a to d but also further unsaturated monomers copolymerizable with methyl methacrylate and the abovementioned (meth) acrylates. These include inter alia alkyl (meth)acrylates, methyl acrylate, ethyl acrylate, butyl acrylate, cyclohexyl (meth)acrylate, norbornyl (meth)acrylate, styrene, substituted styrenes, vinylcyclohexane, vinyl acetate, (meth) acrylic acid, glutaric anhydride, maleic anhydride, n-isopropyl(meth)acrylamide, (meth)acrylamide and acrylonitrile.

The polymer resin optionally contains additives which may be added thereto before or after process step e, preferably before process step e. These include inter alia UV stabilizers, UV absorbers, lubricants, antistats, flame retardants, additives for increasing scratch resistance, antioxidants, light stabilizers, organic phosphorus compounds, weathering stabilizers and/or plasticizers.

In particular according to the invention there are three particularly preferred embodiments in respect of process step e:

In the first embodiment, the suspension polymerization process, a thermoplastically deformable molding material is obtained in which the polymer resin with high monomer conversion, for example not less than 80%, is optionally dried to remove unconverted alkyl methacrylates, other monomers or water. The obtained pearl polymer may then optionally be further degassed in a degassing apparatus, for example a kneader or degassing extruder, and subsequently granulated. The granulates or polymer resin beads may in a subsequent step be subjected to further processing in suitable processing apparatuses to afford the desired molded articles.

In a second embodiment, the solution or bulk polymerization process, a polymer syrup is formed by free-radical polymerization from process step d or from a mixture containing at least one alkyl methacrylate according to process step d. Subsequently, this syrup is optionally degassed in a suitable degassing apparatus to remove unconverted alkyl methacrylates, other monomers or water. The degassed polymer syrup is then optionally granulated. The granulates may in a subsequent step be subjected to further processing in suitable processing apparatuses to afford the desired molded articles.

In a third embodiment, the block polymerization process, polymerization of an optionally solvent-containing mixture is performed up to a solids content of 80% by weight. It is preferable when in this embodiment a solvent-free system is polymerized up to a conversion of less than 80%. It is preferable when the polymerization is performed in a solvent-free system up to a conversion of less than 80%. The polymer syrup is then subsequently poured into a mold. Added substances may be added here. The polymerization of the polymer syrup is then continued to higher conversions in the mold. When the polymer syrup contains no crosslinker monomers or the content of crosslinker monomers is low then the mold may subsequently be thermoformed. At higher contents of crosslinker monomers thermoforming is markedly more difficult.

Optimally the recyclates at least optionally obtained in all three embodiments obtained by degassing are recycled and employed in a further polymerization step e. This can result in the enrichment of byproducts, in particular byproducts of relatively low vapor pressure, during the process. This enrichment in particular in the dimethoxyisobutene (DMIB) and methyl isobutyrate formed in the C2 process results in a further increase in yellow discoloration of the molding in later batches. Thus after a number of recyclates portions of the recyclate must be discarded in order to deplete the recyclate circuit in respect of these byproducts. This in turn leads to a reduction in the overall polymer yield. The process according to the invention now makes it possible, surprisingly, to perform markedly more batches with recycling and reuse of the recyclate and thus to achieve a relevant enhancement of the overall polymer yield.

According to the invention the "C2 process" is to be understood as meaning processes which proceed from a C2 synthesis unit in the synthesis of an alkyl methacrylate. In the context of the present invention it is particularly preferable when in addition the propanal in process step a) is obtained on the basis of ethylene and synthesis gas.

The alkyl methacrylate resins produced according to the invention may find a very wide variety of uses. A distinction should be made on the one hand between transparent and nontransparent, and on the other hand between colored and colorless, moldings which are produced from alkyl methacrylate resins.

Thus transparent moldings, preferably colorless transparent alkyl methacrylate resins, may be employed in particular for producing moldings for use as optically conductive sheets, as headlight lenses, in headlight covers, in covers for light sources, in display covers, in noise barriers or in the construction of greenhouses. Naturally for colorless products in particular, very particularly for transparent colorless products, the yellowness index of the polymer from which the molding has been produced is of particularly high importance so that, surprisingly, with the process according to the invention alkyl methacrylates produced on the basis of C2 raw materials may now also be employed.

Colored alkyl methacrylate resins, in particular those which are filled and thus nontransparent, may be employed for moldings preferably for use in covers, in pillar trim or in decorative strips in passenger car interior and/or exterior applications. However, even for colored alkyl methacrylate resins used in nontransparent form the yellowness index plays a large role in respect of colorfastness, color stability and universal applicability of the color formulations in alkyl methacrylates from other processes.

In addition to the specified process, novel alkyl methacrylates which may be obtained for example as a product from the inventive process steps a to d form part of the subject matter of the present invention. Thus these novel alkyl methacrylates have the feature that the alkyl methacrylate necessarily comprises DMIB as a constituent. The alkyl methacrylate generally also comprises methyl isobutyrate.

These alkyl methacrylates are in particular those producible by means of a very advantageous process which proceeds from a C2 basis instead of a C3 or C4 basis as the base synthesis unit of methacrylate synthesis. C3- or C4-based alkyl methacrylates generally do not comprise this byproduct at all. What is novel about this alkyl methacrylate in particular is that compared to the materials described in the prior art while said alkyl methacrylate does comprise DMIB it comprises it in a not previously known content of less than 300 ppm, preferably less than 150 ppm, very particularly preferably less than 100 ppm, optimally less than 80 ppm and in an exceptionally optimal embodiment less than 20 ppm. In particular, contents of less than 100 ppm are particularly suitable for producing methacrylate resins without visible yellow discoloration.

It is also preferable when the alkyl methacrylate according to the invention further comprises a methyl isobutyrate content of less than 600 ppm, particularly preferably less than 300 ppm and especially preferably less than 100 ppm.

In addition to these alkyl methacrylates, alkyl methacrylate resins produced from a monomer mixture containing 30% to 100% by weight of the alkyl methacrylates according to the invention also form part of the subject matter of the present invention. These alkyl methacrylate resins may moreover be produced from mixtures containing 0% to 70% by weight of further monomers copolymerizable with alkyl methacrylates and/or alkyl methacrylates produced by different processes and optionally 0% to 5% by weight of further added substances.

These alkyl methacrylate resins are preferably characterized in that this alkyl methacrylate resin has a weight average molecular weight determined by gel permeation chromatography (GPC) between 50 000 g/mol and 2 000 000 g/mol. It is especially preferable when the alkyl methacrylate producible according to the invention and used in the alkyl methacrylate resin is methyl methacrylate.

The surprisingly identified negative effect exerted by DMIB in an alkyl methacrylate resin and descendent products produced therefrom is not only yellow discoloration but also reduced thermal stability of the product. This is attributable to a more severe polymer chain degradation during thermal processing and takes effect in particular during processing to afford a molding and during workup of the polymer syrup. It has now been found that, surprisingly, a methacrylate resin according to the invention, a methacrylate according to the invention and a methacrylate resin produced according to the invention do not exhibit either disadvantage.

EXAMPLES

In order to investigate the quality of the alkyl methacrylate resins methyl methacrylate according to process steps a to d from the process according to the invention was polymerized to produce PMMA. Test specimens of 145 mm in length were subsequently produced from the obtained polymer and used to measure the optical properties.

Production of the polymers employed the following raw materials:

Methyl methacrylate from Evonik Industries and from process a to d stabilized with 3 ppm of hydroquinone monomethyl ether.

N-dodecylmercaptan was obtained from Chevron Phillips and tert-butylperisononanoate was obtained from United Initiator GmbH.

For polymerization the reactants were continuously supplied to a continuously operated stirred tank having an internal volume of 2.4 L ensuring that the polymerization temperature is always in the range between 120° C. and 150° C. The polymerization proceeded up to a monomer conversion of 55%. The residual monomers of the output polymer syrup were continuously degassed in an extruder at 250° C. The thus obtained polymer strands of the degassed polymer melt were cooled in air and subsequently granulated.

Reactor Feed for the Polymerization
 3500 g/h of methyl methacrylate
 7.0 g/h of n-dodecylmercaptan
 2.0 g/h of tert-butylperisononanoate To evaluate the optical quality of the polymers polymer granulate was pressed at 220° C. and 50 bar of pressure to afford moldings from which rods having dimensions of 10 mm×10 mm×145 mm were then cut and the surfaces polished by means of a diamond polisher.

The yellowness index Y.I. and D65/10° transmission coefficient of this molding were measured over the 145 mm length in a Varian Cary 5000 instrument.

For the specific examples the respective byproduct proportions of DMIB and methyl isobutyrate in the monomers from process step d are also reported. The MMA batches employed in examples 3 and 4 serve as a reference. This particular MMA was produced by means of a C3 process and accordingly contains neither DMIB nor methyl isobutyrate.

Example 1

Methyl methacrylate from process a to d with
<6 ppm of DMIB; 230 ppm of methyl isobutyrate
(after process step d)

The following process was employed in particular in relation to process step c:

The output from process step b, reactor II was passed into the process step c, reactor III for workup. Reactor III was in the form of a continuously operated stirred tank with a decanter connected downstream.
pH in stirred tank: 2
Residence time in stirred tank: 60 min
Temperature in stirred tank: 25° C.
Residence time in decanter: 60 min
Temperature in decanter: 25° C.

Feeds into Reactor III Process Step c:
1. Acidic Aqueous Phase:
   Sulfuric acid 100% H2SO4=1.05 g/h
   Water=106.05 g/h
2. Feed from Process Step b:
   MMA=56.11% by weight
   Methanol=13.67% by weight
   DMIB=1659 ppm
   Methyl isobutyrate=305 ppm
   Organic residues=18.57% by weight
   H2O=11.44% by weight
   Total flow: 150 g/h
Composition of Crude Alkyl Methacrylate after Process Step c:
   DMIB<6 ppm (1 ppm in organic phase)
   Organic phase methyl isobutyrate=449 ppm
   Aqueous phase methyl isobutyrate=14 ppm Example 2 (Comparative Example)

Methyl methacrylate from process a, b and d, without process step c with
1550 ppm of DMIB; 475 ppm of methyl isobutyrate Example 3 (Reference Example)

Methyl methacrylate from Evonik Industries admixed with
1000 ppm of DMIB; 50 ppm of methyl isobutyrate Example 4 (Reference Example)

Methyl methacrylate from Evonik Industries as reference with
<5 ppm of DMIB; 50 ppm of methyl isobutyrate In example 1 MMA according to process steps 1 a to d was employed and a low yellowness index and a high transmission achieved. The content of DMB is low at less than 6 ppm. Example 2 (comparative example) employs MMA according to process steps a, b and d, but without the workup step c. The content of DMIB is higher than in example 1 at 1550 ppm, thus resulting in a higher yellowness index and a lower transmission of the polymethacrylate resin.

In examples 3 and 4 (reference examples) Evonik MMA from the ACH process in which no DMIB is formed was used in each case. Once with an artificially added 1000 ppm of DMIB and in example 4 without any addition of DMIB. Example 3 again shows a higher yellowness index and a lower transmission than example 4.

The condensates of the degassed residual monomers were, with high DMIB contents in the employed MMA, very yellow, example 2 and example 3.

TABLE 1

Comparison of results

| | MMA | DMIB [ppm] | Methyl isobutyrate [ppm] | Y.I. 145 mm Polymer [–] | Transmission D65/10° Polymer [%] | Y.I. 10 mm Condensate [–] |
|---|---|---|---|---|---|---|
| Example 1 | Process a-d | <6 | 230 | 4.1 | 92.2 | 3.2 |
| Example 2 | Process a-d/without c | 1550 | 475 | 12.0 | 91.5 | 9.8 |
| Example 3 | Evonik Ind. | 1000 | 50 | 7.0 | 91.8 | 8.7 |
| Example 4 | Evonik Ind. | <1 | 50 | 4.1 | 92.7 | 3.5 |

The respective yellowness indices for the condensates of the degassed polymer syrups are affected by DMIB concentration in the employed alkyl methacrylate. Thus the yellowness indices of the vacuum condensates from examples 1 and 4 are very low while the vacuum condensates of examples 2 and 3 are markedly higher.

The invention claimed is:

1. A process for producing an alkyl methacrylate resin, comprising:
   a. producing methacrolein in a reactor I,
   b. oxidatively esterifying the methacrolein in the presence of an alcohol, oxygen and a heterogeneous noble metal-containing catalyst at a water content between 0.1% and 10% by weight and a pH between 5 and 8 in at least one reactor II, to obtain a reactor output,
   c. after-treating the reactor output from the at least one reactor II in a reactor III, to obtain a crude alkyl methacrylate,
   d. isolating and purifying the crude alkyl methacrylate from reactor III, and
   e. polymerizing the alkyl methacrylate from process step d or a mixture containing alkyl methacrylates from process step d to obtain an alkyl methacrylate resin,
   wherein in process step c, in the reactor III, a water content is at least 0.5% by weight higher than in the at least one reactor II, an alcohol concentration is lower than in the at least one reactor II, and a pH is set to between 0.5 and 6 and thus at least 0.5 lower than in the at least one reactor II.

2. The process according to claim 1, wherein process step a, in reactor I, is a reaction of propanal with formaldehyde in the presence of at least one acid and optionally of an amine.

3. The process according to claim 1, wherein the alcohol is methanol and the alkyl methacrylate is methyl methacrylate (MMA).

4. The process according to claim 1, wherein in process step c, an organic and/or a mineral acid are added to the reactor III to adjust the pH, wherein in the reactor III, dimethoxyisobutene is cleaved with water to obtain methacrolein and methanol.

5. The process according to claim 1, wherein in process step e,
an alkyl methacrylate resin is produced by bulk, emulsion, suspension or solution polymerization from the alkyl methacrylate or from the mixture containing at least one alkyl methacrylate from process step d, and
subsequently said alkyl methacrylate resin is processed into a molding material or in admixture with other components processed into a molding material.

6. The process according to claim 1, wherein in process step e, a syrup is formed by free-radical polymerization up to a solids content of less than 80% from the alkyl methacrylate from process step d or from the mixture containing at least one alkyl methacrylate according to process step d, said syrup is poured into a mold and subjected to final polymerization therein.

7. The process according to claim 1, wherein in process step e, a syrup is formed by free-radical solution or bulk polymerization from the alkyl methacrylate from process step d or from the mixture containing at least one alkyl methacrylate according to process step d, said syrup is optionally degassed, optionally granulated and processed into a molding.

8. The process according to claim 1, wherein in process step e, a polymer resin is formed by free-radical suspension polymerization at a conversion of at least 80% of monomers from the alkyl methacrylate from process step d or from the mixture containing at least one alkyl methacrylate according to process step d, said polymer resin is optionally dried, optionally degassed, optionally granulated to obtain a granulate or polymer resin beads, and from a granulate or polymer resin beads, moldings are produced.

9. The process according to claim 6, wherein a recyclate obtained in a degassing step is recycled and supplied to the mixture of alkyl methacrylates in process step e.

10. The process according to claim 4, wherein in process step c, sulfuric acid is added to the reactor III to adjust the pH, and a liquid phase in reactor III has a temperature between 0° C. and 140° C.

11. The process according to claim 4, wherein reactor III is a distillation column into the bottom of which the acid and optionally additional water are introduced and in which methacrolein and portions of a remaining alcohol are separated from the crude alkyl methacrylate at a temperature between 50° C. and 100° C.

12. The process according to claim 4, wherein the reactor III is a phase separator into whose aqueous phase the acid and optionally additional water are introduced and in which an aqueous phase containing a remaining alcohol is separated from an organic phase containing the crude alkyl methacrylate at a temperature between 0° C. and 100° C.

13. The process according to claim 4, wherein the reactor III is a tubular reactor in which the reactor output from the at least one reactor II having an internal temperature between 50° C. and 140° C., the acid and optionally additional water are mixed, and this mixture is subsequently passed into a distillation column or a phase separator.

14. The process according to claim 4, wherein the reactor III is a continuously operated stirred reactor in which the reactor output from the at least one reactor II having an internal temperature between 50° C. and 140° C., the acid and optionally additional water are mixed and this mixture is subsequently passed into a distillation column or a phase separator.

15. The process according to claim 1, wherein the isolation and purification stages comprise at least one phase separator, at least one high boiler column, at least one low boiler column and optionally at least one crystallization chamber, and wherein said at least one phase separator, said at least one high boiler column, said at least one low boiler column, and optionally said at least one crystallization chamber are traversed in series.

16. A method for producing a transparent article, the method comprising:
molding the alkyl methacrylate resin produced by the process according to claim 1 into a transparent article,
wherein the transparent article is at least one selected from the group consisting of optically conductive sheets, headlight lenses, headlight covers, covers for light sources, display covers, noise barriers, and construction materials of greenhouses.

17. A method for producing a colored article, the method comprising:
molding the alkyl methacrylate resin produced by the process according to claim 1 into a colored article,
wherein the colored article is at least one molding in covers, in pillar trim, or in decorative strips in passenger car interior and/or exterior applications.

* * * * *